(12) United States Patent
Ditto

(10) Patent No.: US 7,022,109 B1
(45) Date of Patent: Apr. 4, 2006

(54) PAIN ABATEMENT CATHETER SYSTEM

(76) Inventor: Deborah L. Ditto, 6820 Hwy. 70 South, Apartment 305, Nashville, TN (US) 37221

( * ) Notice: Subject to any disclaimer, the term of this patent is extended or adjusted under 35 U.S.C. 154(b) by 322 days.

(21) Appl. No.: 10/191,156

(22) Filed: Jul. 9, 2002

Related U.S. Application Data

(60) Provisional application No. 60/303,663, filed on Jul. 9, 2001.

(51) Int. Cl.
*A61M 5/178* (2006.01)

(52) U.S. Cl. .................. 604/158; 604/164.01; 604/506

(58) Field of Classification Search ................ 604/264, 604/523, 93.01, 158, 161, 164.01, 164.05, 604/164.06, 164.07, 164.08, 164.09, 164.1, 604/164.11, 164.12, 164.13, 500, 506, 508
See application file for complete search history.

(56) References Cited

U.S. PATENT DOCUMENTS

| | | | |
|---|---|---|---|
| 4,827,941 A * | 5/1989 | Taylor et al. ................ 600/434 |
| 4,917,670 A | 4/1990 | Hurley et al. |
| 4,973,312 A | 11/1990 | Andrew |
| 4,985,022 A | 1/1991 | Fearnot et al. |
| 4,994,036 A | 2/1991 | Biscoping et al. |
| 5,085,631 A | 2/1992 | Leighton |
| 5,106,376 A | 4/1992 | Mononen et al. |
| 5,215,105 A | 6/1993 | Kizelshteyn et al. |
| 5,238,004 A * | 8/1993 | Sahatjian et al. ........... 600/585 |
| 5,312,341 A * | 5/1994 | Turi ...................... 604/103.05 |
| 5,470,318 A | 11/1995 | Griffith, III et al. |
| 5,490,845 A | 2/1996 | Racz .......................... 604/266 |
| 5,562,722 A | 10/1996 | Racz .......................... 607/117 |
| 5,800,407 A | 9/1998 | Eldor |
| 5,810,788 A | 9/1998 | Racz .......................... 604/272 |
| 5,899,891 A | 5/1999 | Racz .......................... 604/280 |
| 6,190,372 B1 | 2/2001 | Racz .......................... 604/534 |

\* cited by examiner

*Primary Examiner*—Kevin C. Sirmons
(74) *Attorney, Agent, or Firm*—Caesar, Rivise, Bernstein, Cohen & Pokotilow, Ltd.

(57) ABSTRACT

A pain abatement catheter system particularly suited for treatment within the epidural space of a patient which includes an epidural introducer assembly, an epidural catheter and a steerable epidural guidewire assembly. The introducer assembly provides a one-piece introduction into the epidural space and includes an elongated introducer needle, an inner stylet, and a flexible outer sheath with a hub. The improved epidural catheter may be safely introduced into the epidural space under fluoroscopic guidance and can be effectively steered through tortuous anatomy, adhesions, or scar tissue for the purpose of delivering medications or contrast dyes to highly selective areas of the epidural space including nerve-root-sleeve injections. The epidural catheter/hub assembly is advanced over a soft atraumatic tip guidewire which significantly decreases the risk of device breakage, nerve root damage, or spinal cord injury. The improved catheter also increases efficacy, maneuverability, and safety in the diagnosis and intervening treatment of acute and chronic back and limb pain. The steerable epidural guidewire assembly allows for safely introducing a guidewire into the epidural space through a flexible sheath cannula and effectively maneuvering the catheter into highly specific areas while reducing the risk of epidural, nerve root, or spinal cord injury.

20 Claims, 5 Drawing Sheets

PAIN ABATEMENT CATHETER SYSTEM

RELATED APPLICATIONS

This application claims the benefit of the filing date of the following provisional patent application, the entire disclosure of which is incorporated by reference herein: AS No. 06/303,663, entitled STEERABLE EPIDURAL CATHETERIZATION SYSTEM, filed on Jul. 9, 2001.

BACKGROUND OF THE INVENTION

1. Field of the Invention

The present invention relates to a pain abatement catheter system ("PACS") to be used in treatment and diagnosis within the epidural space of a patient. More specifically, the invention relates to a system of components including a percutaneous introducer assembly, an epidural catheter and an epidural guidewire assembly capable of being steered within the epidural space.

Together, these components define a pain abatement catheter system, PACS, which minimizes procedure time, reduces risk of injury and complications to the patient, provides for greater patient comfort, simplifies use by the practitioner and lessens practitioner exposure to radiation. The three principal components of the present invention, PACS, are discussed in seriatim.

2. Description of the Prior Art

Past problems in Placement or Introducing a Catheter Percutaneously The treatment of intractable nerve pain has traditionally necessitated the percutaneous introduction of large gauge (15–16 g RK) needles into the epidural space whereby the catheter is inserted through the lumen of the needle and into the epidural space. An inherent problem of inserting a catheter into the epidural space in such manner is the risk of catheter shearing due to the piercing tip of the epidural needle. Moreover, advances in the treatment of specific nerve root sleeves require the catheter, once introduced into the epidural cavity, to be advanced and retracted which increases the risk of catheter shearing during the procedure and thereby exposes the patient to unnecessary surgery.

Implantable lead stimulators for the brain and spinal cord have been used for some time in the treatment of chronic pain, spinal cord injury, multiple sclerosis, cerebral palsy, and many other neurological disorders. In addition, spinal cord stimulation has been proposed to promote recovery from injury, to accelerate nerve regeneration, and to induce locomotion. At present, such neural stimulation electrodes and leads are introduced usually for the purpose of pain relief through an epidural needle in the traditional manner and placed into the epidural space in specific locations. The epidural needle is used to introduce, steer, and manipulate these devices within the epidural space. In the present state of the art whereby manipulation of catheters and devices takes place within the lumen of the epidural needle, device damage often results in shearing which can lead to serious patient injury.

Prior Art Catheters and Problems with their Percutaneous Introduction

The Racz Tun-L-Kath of Racz Tun-L-XL catheters by EPIMED are the current standard for use in lysis of epidural adhesions (epidural neuroplasty) and in catheter placement in patients presenting scar tissue or other difficult placements. Many problems and risks are associated with the Racz catheter. For instance, the Racz catheter is caused to "dwell" in the epidural space through a tubular needle which carries a significant risk of catheter damage due to the piercing tip of the epidural needle. In fact, the manufacturer states "DO NOT RETRACT OR REMOVE CATHETER WITH NEEDLE IN PLACE"; however, this is frequently done in practice due to the need to steer the catheter.

The difficult-to-use multi-piece Racz design consists of a 24" epidural catheter with a stainless steel spring coil end, a detached luer fitting hub, and a stainless steel inner stylet. Its use requires multiple steps: To inject contrast dye or medications, the inner stylet must first be removed and the luer fitting hub correctly placed on the catheter, which is time consuming and cumbersome. After the medications or dyes have been administered, the hub must be removed and the inner stylet replaced to advance the catheter within the epidural space. Each of these steps increases the risk of complications and patient injury. The spring coil end, in particular, has a dual risk of breakage and of being pierced by the inner stylet which can result in serious damage to the epidural lining, nerve roots, spinal cord, or an unnecessary surgical procedure for the patient.

Risks to the Practitioner Using Prior Art Catheters

The Razz 24" catheter length places the practitioner extremely close to the radiation source, and does not provide enough distance for a radiation protection lead barrier. The short catheter length necessitates the practitioner's hands to be within inches of the radiation beam, and at times directly in the field of radiation. The effects of low dose fluoroscopic radiation are relatively unknown, although it is known to damage delicate organs such as the eyes and thyroid. Therefore, it is extremely important to follow the three cardinal rules of radiation protection: time, distance, and shielding. Time of exposure should be minimized; distance from the radiation source should be maximized; and a barrier lead shield should be placed between the radiation source and the practitioner. Because radiation is heavier than the atmosphere, a small increase in distance, even inches, makes a vast difference in the amount of scattered radiation received. In fact, when distance from the radiation source is doubled, the amount of scatter radiation is reduced by fifty percent.

Prior Art Guiding Devices

Traditionally, epidural catheters such as the Racz epidural catheter manufactured by EPIMED and presently in use for lysis of epidural adhesions have employed an inner stylet to aid in control and to make the catheter stiffer during insertion and placement. The inner stylet would then be removed and discarded as it was no longer needed. A vexing problem with such practice is that prior to injecting medication or contrast dye into the epidural space the inner stylet must be removed. Likewise, advancement of the catheter requires the inner stylet to be replaced. Such frequent manipulation of the inner stylet during interventional pain procedures is problematic. Inner stylet "freezing" is a frequent occurrence causing the catheter and inner stylet to be forcibly pushed or pulled resulting in the risk of patient injury. In these instances, the catheter must be discarded and a new one introduced percutaneously necessitating removal of the old catheter through the lumen of the needle.

SUMMARY OF THE PRESENT INVENTION

One aspect of the present invention involves a novel system for providing, introducing, guiding, manipulating and removing medical devices and administering medications or dyes within the epidural space of a patient for the purpose of easing patient pain in a safe and time-efficient manner. This and other aspects are achieved by the components of the present pain abatement catheter system (PACS)

which includes an epidural introducer assembly, an epidural catheter, and a steerable epidural guidewire assembly.

Epidural Introducer Assembly ("EIA")

Another aspect of the present invention is achieved by the epidural introducer assembly which consists of an introducer needle, an inner stylet and a flexible outer sheath which may have side ports and graduated outer makings to indicate insertion depth. These three components of the EIA are assembled such that they are introduceable into the epidural space as a single unit by locking means such that the inner stylet rests within the lumen of the introducer needle and the needle in turn sits within the interior cavity of the flexible outer sheath.

The assembly once placed percutaneously may be unlocked such that the inner stylet is removed to confirm placement. Following, the sheath is unlocked and the needle removed leaving the sheath in the epidural space to provide safe passage of catheters and devices. In this manner, the risk of catheter shearing and patient injury inherent in the prior art is substantially eliminated.

Epidural Catheter

Another aspect of the invention is to provide an epidural catheter which may be a reinforced single piece unit or a multiple piece unit having an open-ended distal end or with side holes and a proximal end connected to a fitting for administration of medication and or media to facilitate patient comfort and procedure time reduction. A further aspect of the invention is to provide an epidural catheter of sufficient length so as to minimize radiation exposure of the clinicians present during the pain abatement catheter procedure. The epidural catheter of the present invention has as an additional aspect the reduction or elimination of catheter shearing or abrasion when advanced or withdrawn during a procedure.

In view of drawbacks such as shearing associated with the prior art epidural catheters, an aspect of the present invention is to provide a novel catheter/hub assembly where the epidural catheter can be precisely steered through the epidural space under fluoroscopic guidance with minimal risk of complications such as catheter breakage or shearing, nerve damage, or spinal hematoma.

A further embodiment of this invention employs catheter sideholes for dispersion of medication. This technique may decrease the pain and pressure associated with injection of fluids into the epidural space through an open distal end, and may reduce the risk of intracranial hemorrhage associated with rapid high volume injections by means of smaller more controlled injections.

Additionally, a manifold adapter is a further embodiment that may be formed of a suitable transparent thermoplastic resin and will provide for dispersion of medications and contrast dye with the ability to simultaneous leave a steerable guidewire in place during injection. This embodiment of an adaptor eliminates the problematic multi-step method risks and difficulty of use of the prior art. In using this method, the practitioner is able to guide the catheter while administering small "puffs" (0.25 to 0.50 ml) of contrast dye or medications. The manifold adapter of the present invention thus eliminates the practitioner need for prior art catheter bolus injections (4.0 to 6.0 ml) which are typically administered.

Steerable Epidural Guidewire Assembly ("SEGA")

One aspect of the present invention involves providing a novel steerable atraumatic tip epidural guidewire/toquing device and related methods. The guidewire assembly of the present invention comprises a manifold adapter, a torquing device, and an elongated radiopaque guidewire. The steerable guidewire assembly can be accurately advanced into areas with spinal stenosis, scar tissue, and adhesions. Once the guidewire is steered into the locality, the epidural catheter is advanced over the guidewire. In this manner, the guidewire may be used to safely advance an epidural catheter through tortuous anatomy under fluoroscopic guidance.

BRIEF DESCRIPTION OF THE DRAWINGS

Epidural Introducer Assembly ("EIA") Drawings

The advantages and features of the present invention will be more readily apparent from following the detailed description of the preferred embodiments illustrated in the drawing figures wherein.

Epidural Catheter Drawings

Figure 6:
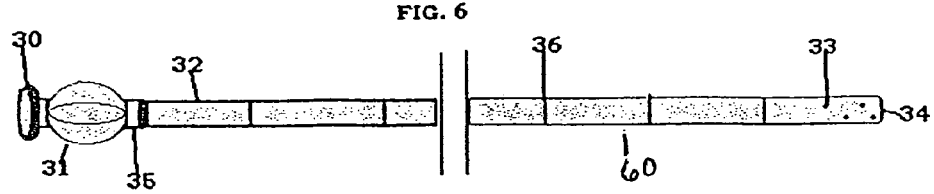
Figure 7:
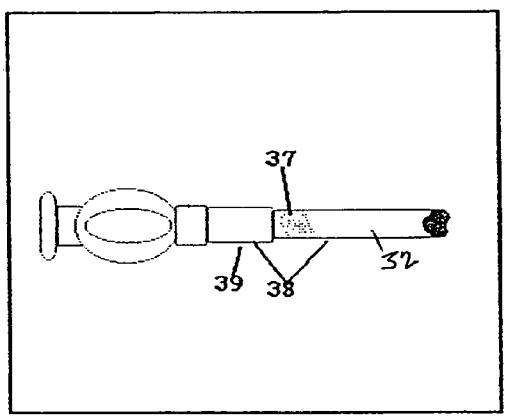
Figure 8:
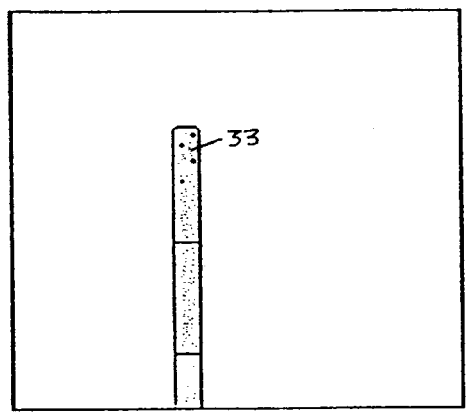

FIG. 6 is a side view of the elongated epidural catheter;

FIG. 7 is a partial sectional view of the catheter shaft;

FIG. 8 is a perspective representation of the catheter tip configuration presenting side holes;

Stearable Epidural Guidewire Assembly ("SEGA") Drawings

Figure 9:
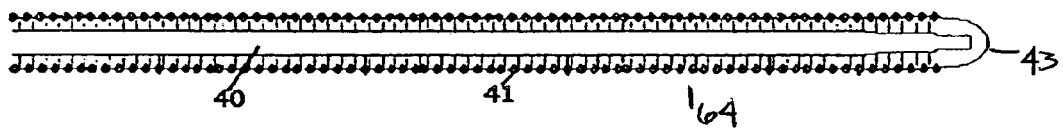
Figure 10:
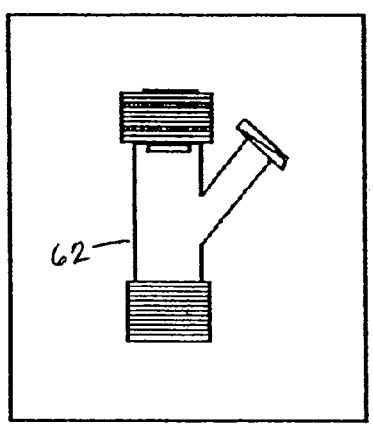

FIG. 9 is a side view of the epidural guidewire;

FIG. 10 is a side view of the manifold adapter; and

Figure 11:
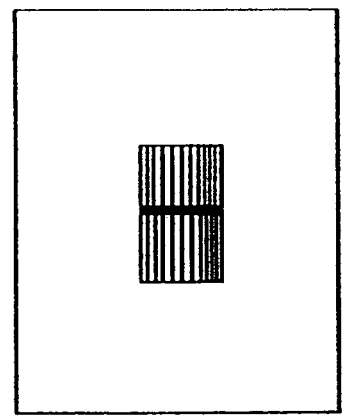

FIG. 11 is a side view of the torquing device.

DESCRIPTION OF THE PREFERRED EMBODIMENTS OF THE INVENTION

Epidermal Introducer Assembly ("EIA")

Figure 1:
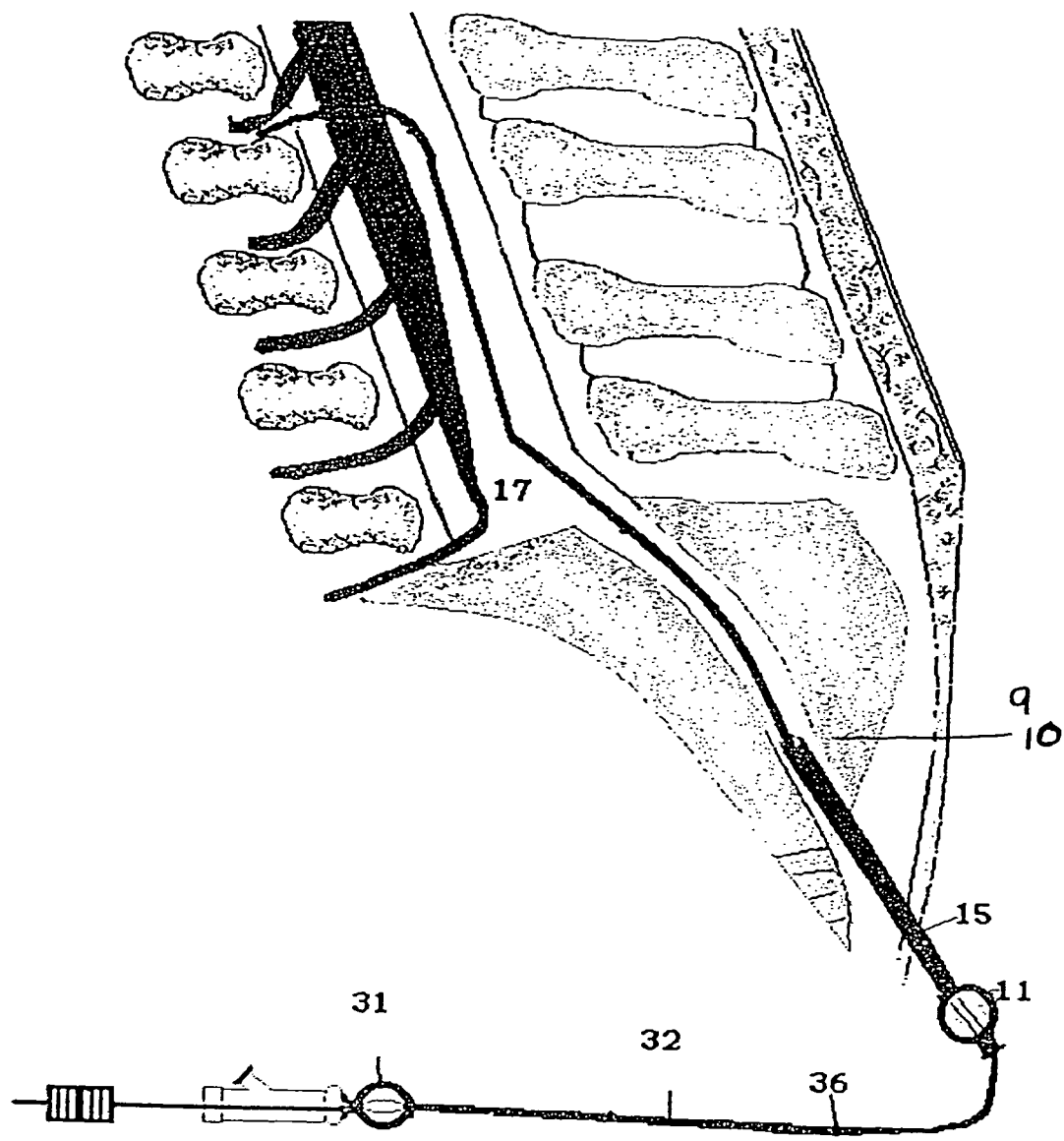
FIG. 1 is a perspective representation of the advancement of a flexible elongated catheter into the epidural space through a flexible outer sheath.
Figure 12:
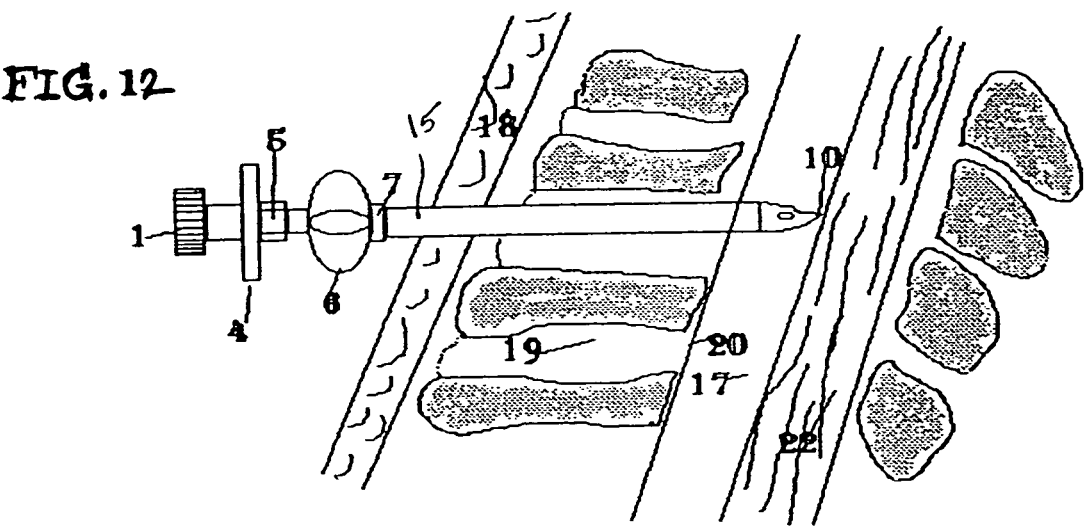
Figure 13:
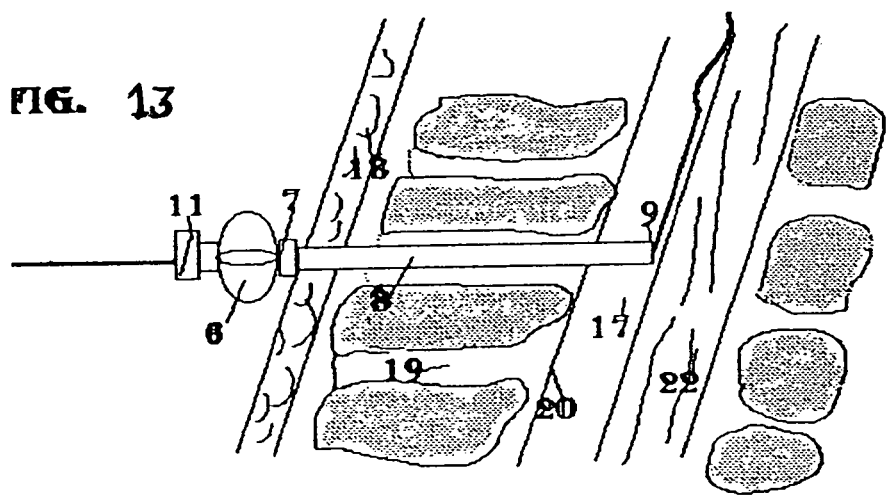

FIGS. 12 and 13 illustrate the procedure depicted in FIG. 1 for introducing a flexible catheter into the epidural space 17 for the treatment of pain in the manner described above. In FIG. 1 the flexible outer sheath 15 is shown with the assembly penetrating the subcutaneous fascia through the sacral hiatus.

Penetration and correct placement into the epidural space 17 can be confirmed by two methods. One, the inner stylet 1 is removed and the needle lumen 12 is filled with saline solution and slowly advanced until the saline rapidly drains when penetration is achieved. Alternatively, contrast dye may be injected and correct placement confirmed under fluoroscopic radiation.

According to FIG. 1, the assembly is advanced through the sacral hiatus (caudal entry method) or between vertebrae until the distal tip 9 is positioned in the epidural space 17. The caudal entry method is a preferred method of entry to the epidural space for several reasons: (1) it is relatively easily achieved; (2) there is minimal risk of inadvertent dural puncture; (3) there is minimal risk of intraneural injection and neural trauma; and (4) the assembly may be rotated to the affected side thereby eliminating the need for an additional percutaneous entry.

In accordance with the improvements of the present invention, a novel epidural introducer assembly is provided where the assembly is advanced as a one-piece entry into the epidural space 17 as shown in FIG. 12. FIG. 13 illustrates where the introducer needle 12 has been unlocked by a turning motion and the introducer needle 12 and inner stylet 1 removed leaving the flexible outer sheath 15, in place. Safe passage of devices is provided within the flexible outer sheath 15, thus eliminating the risk of catheter damage and shearing. FIG. 1 thus illustrates the operative steps of the procedure for attaining access to the epidural space 17, and the facilitation of safe manipulation of catheters within the sheath 15 in the epidural space 17.

Figure 2:
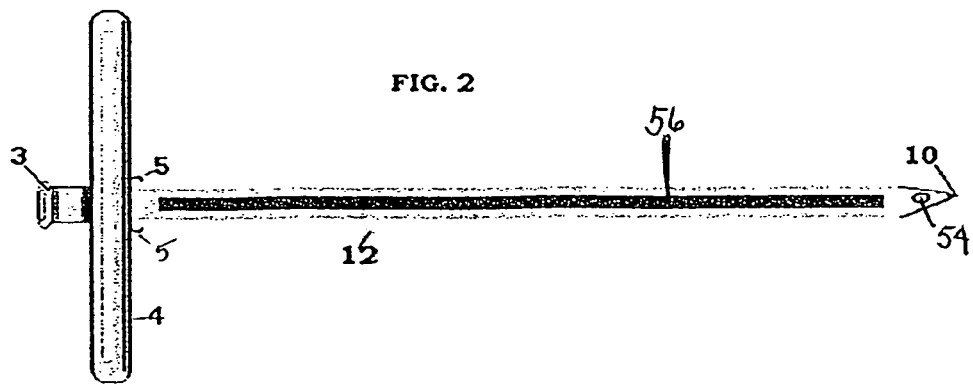
FIG. 2 is a side view of the epidural introducer needle.

Referring now to FIG. 2, it depicts the elongated introducer needle 12 which includes a stainless steel needle typically between 14 and 18 guage. Attached to the proximal end of the needle are wide finger engageable wings 4 coupled to a luer tapered hub 3 with locking mechanisms for both the inner stylet 1 distally and the flexible sheath on the distally oriented surface of the wings 4, whereby L-shaped appendages 5 lock to the sheath's luer tapered hub 11. The distal tip 10 of the needle 12 possesses an elongated beveled Huber point side opening 54 with a lumen 56 extending therebetween.

Figure 3:
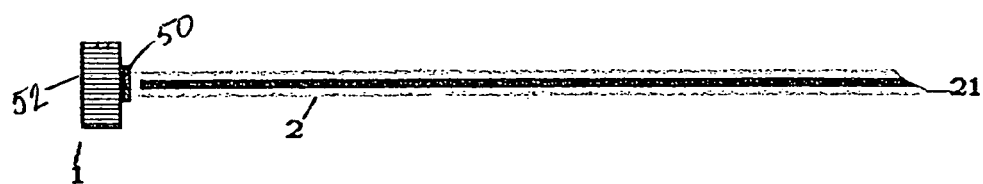
FIG. 3 is a side view of the inner stylet.

Turning now to FIG. 3, it illustrates a side view of the inner stylet 1 which may be constructed of stainless steel 2. The proximal end of the stylet 1 is connected to a lug 50 that possesses a luer fitting cap 52. When the inner stylet 1 is locked to the introducer needle luer tapered hub 3, the sharpened tip 21 matches the beveled opening of the distal tip 10 of the introducer needle 12.

Figure 4:
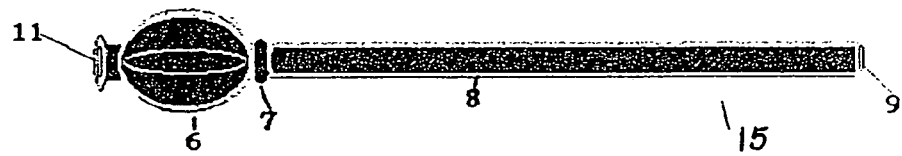
FIG. 4 is a side view of the flexible outer sheath with a hub in accordance with the improvements of the present invention.

Referring now to FIG. 4, the flexible outer sheath 15 is described in greater detail. The hub 6 may be constructed of molded nylon material having a luer tapered end 111 which locks into the appendages 5 of the introducer needle 12. Connected to the hub 6 by strain relief is a flexible sheath cannula 8 constructed of a high quality polymer blend material that allows bending without kinking. The outer coating of the cannula 8 may be lubricious in nature as with hydrophilic coating to allow transition during insertion. The sheath cannula 8 presents a rounded taper distal end 9 to minimize tearing or fishmouthing of the sheath cannula 8, thus reducing puncture site trauma and epidural damage. A further embodiment of the invention (not shown) is a pre-split sheath so that the sheath can be pulled back and peeled away to leave the catheter in the epidural space for long term injection.

Figure 5:
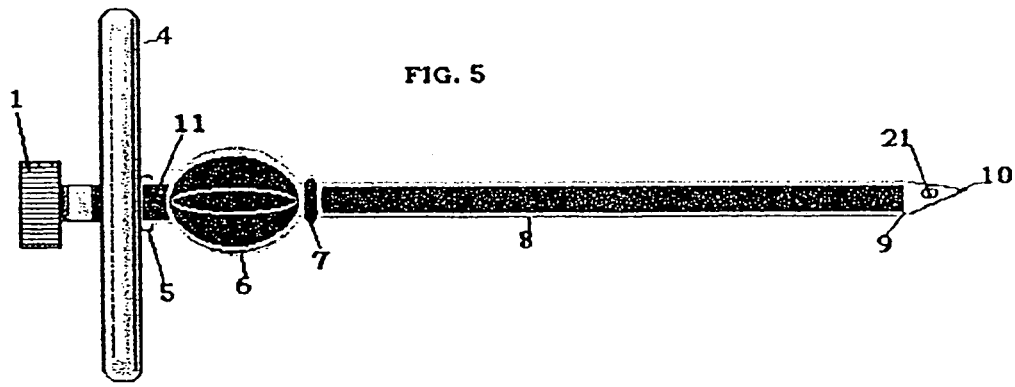
FIG. 5 is a side view of the assembly of the introducer needle, the inner stylet and the flexible outer sheath in relation to each component.

Turning now to FIG. 5, the assembly of the inner stylet 1, introducer needle 12, and flexible outer sheath 15 is depicted. The inner stylet 1 is inserted into the lumen 56 of the introducer needle 12 so that the inner stylet can be rotated until it sits in the position depicted in FIG. 5. The sheath 15 is locked in a similar method where the flexible outer sheath hub luer taper 11 is locked by two L-shaped appendages 5 extending from the distally oriented face of the introducer wings 4.

The above described method, installation, and access to the epidural space is greatly facilitated by the use of fluoroscopic radiation and other known techniques by those skilled in the art. Accordingly, the various elements of the present invention are preferably formed of radiopaque material. Further, any one of the components oh the present invention may be comprised of any one of the following materials: braided Peebax 31 pic continuous, braided peebax 45 pic continuous, braided polyurethane continuous, non braided Peebax, and braided Peebax with polytetra fluoroethelened liner.

Epidural Catheter

In accordance with the improvements of the present invention, a novel catheter/hub assembly and method are provided where the assembly is advanced as a one-piece assembly. In the drawings, FIG. 1, FIG. 6–FIG. 8 illustrate a presently preferred epidural catheter/hub assembly for use in the procedure depicted in FIG. 1 for introducing a catheter 60 into the epidural space 17.

The epidural catheter FIG. 6 comprises a finger-engageable luer tapered hub 30 which may be constructed of a molded nylon material. The inner diameter of the catheter hub 30 is equivalent to the inner diameter of the catheter shaft 32 and thus not a limiting factor during injection. The hub 30 provides a tight seal between the catheter 60 and any auxiliary equipment and may be constructed of a molded nylon material. The luer tapered hub 30 is securely connected to the catheter shaft 32 by means of strain relief 35. The strain relief 35 one-piece catheter design reduces the risk of catheter breakage and, therefore, the risk of complications are minimized.

Turning now to FIG. 7, a side view of the catheter shaft 32 is shown. A stainless steel wire braiding 37 of the catheter shaft 32 provides maximum torque and pushability and will minimize the incidence of kinking. The catheter body 38 may be constructed of a suitable material, such as a polyurethane blend, providing superior shape retention and handling and will maintain luminal patency during catheter manipulation and exchange. Further suitable materials are any braided or non-braided Peebax materials with or without a poly tetra fluoro catheter liner.

The catheter shaft may employ a slick coating, such as polytetrafluoroethelene lining 39 for the inner and outer surface to reduce guidewire friction and tissue drag. Another embodiment of the invention employs a lubricious surface (i.e. hydrophilic coating) to further facilitate entry into diseased areas of the spinal canal.

Referring now to FIG. 8, a presently preferred catheter tip 34 configuration is shown. The distal tip 34 of the catheter 60 may be slightly tapered for improved transition during insertion and maneuvering within the epidural space 17.

The epidural catheter 60 employs sideholes 33 in the distal tip 34 to disperse medications and may decrease patient discomfort due to the pressure of injection. The catheter sideholes 33 in conjunction with the manifold adapter 62 depicted in FIG. 10 allow medication and contrast injection while concurrently allowing the guidewire 64 to remain within the epidural space 17. This method may reduce the risk of intracranial hemorrhage and epidural hematoma by decreasing the force of injection. The manifold adapter 62 depicted in FIG. 10 will further reduce these risks by allowing smaller more controlled "puffs" of contrast and medications. By comparison, the prior art method necessitates injecting larger volumes all at once since the inner stylet (prior art stylet not shown) had to be replaced to advance the catheter. The present invention eliminates the prior art steps needed to guide a catheter within the epidural space 17. The catheter 60 of the present invention allows for multiple, simultaneous treatment, such that the lumbar, thoracic, and cervical spine may all be treated during a single procedure.

The epidural catheter 60 of the present invention may be approximately 3.6 ft. in diameter and have 100 cm. of useable catheter length. The catheter shaft may be approximately 0.049" outer diameter and 0.036" inner lumen diameter. The additional catheter length provides added radiation safety for the practitioner, and allows a lead shield to be placed between the practitioner and the radiation source. The additional catheter length allows multiple levels of treatment using the caudal entry method. Obviously, variations may occur based on needs and use as with the scape of the present invention.

The above described use of the present invention is greatly facilitated by fluoroscopic radiation and to that end the various elements of the present invention are preferably formed of radiopaque materials. Further radiopaque markers 36 at the distal tip and every 10 cm facilitate visualization and accurate diagnosis and treatment.

Stearable Epidural Guidewire Assembly (SEGA)

In, FIG. 1 and FIG. 9–FIG. 1 is shown a presently preferred steerable epidural guidewire/assembly device for use in interventional and diagnostic pain procedures.

FIG. 9 depicts the straight epidural guidewire 64. A one-piece stainless steel core wire 40 covered by stainless steel alloy coils 41 provides 1:1 torque control to the distal tip 43.

The steerable epidural guidewire may employ a variety of characteristics, such as a tapered tip and/or a stiff atraumatic tip to permit crossing of obstructions due to adhesions in the epidural space. The guidewire assemlby may consist of a braided or non-braided Peebax material and may include a spra-coated or pretreated guidewire which may or may not be radiopaque.

Further, the guidewire length may be from 120 cm to 140 cm and may be radiopaque for purposes of fluoroscopic guidance.

The foregoing description of the embodiments of the present invention may be modified by those skilled in the art to adapt to various conditions of use and are not meant to be limiting in degree on scope.

The invention claimed is:

1. A catheter system for diagnosis and treatment in an epidural space involving an epidural introducer assembly which comprises the following components:
   (a) a flexible outer sheath having distal and proximal ends wherein said proximal end terminates in a hub and a luer tapered end, said hub is connected to a flexible cannula rounded at its distal end and wherein a cylindrical bore defines the interior of said sheath;
   (b) an introducer needle having proximal and distal ends and an interior bore and finger engageable wings attached at said proximal end, said wings having a distal and proximal face, said wings also having locking means on the distal face and a luer tapered hub attached on the proximal face of the wings, said introducer needle having a predetermined length and being adapted to be inserted and fixed by locking means into the interior bore of said flexible outer sheath and having at its distal end a cutting tip adapted for percutaneous introduction; and
   (c) an inner stylet having a predetermined length and having proximal and distal ends and being adapted to be inserted within the interior bore of said introducer needle and wherein said proximal end is attached a lug having a luer fitting cap and at which distal end is a tip configured and dimensioned to fit between the contours of the cutting tip of the distal end of said introducer needle.

2. The catheter system of claim 1, wherein the epidural catheter comprises a catheter having distal and proximal ends, the proximal end having a finger-engageable luer tapered hub and the distal end having a tip adapted for administration of medications or devices.

3. The catheter system of claim 1 wherein the steerable epidural guidewire assembly comprises:
   (a) a single length of core wire having proximal and distal ends, the distal end presenting a tip and dimensioned to be variably positioned with the hollow core of the epidural catheter and a surface presenting coil adapted for steering of said core wire;
   (b) a torquing device; and
   (c) a manifold adaptor.

4. The epidural introducer assembly of claim 1 wherein the flexible outer sheath has side ports.

5. The epidural introducer assembly of claim 1 wherein the flexible outer sheath has graduated outer markings to indicate depth of insertion.

6. The epidural introducer assembly of claim 1 wherein the flexible outer sheath is adapted to be pulled away and disengaged from said epidural catheter to permit long term injection via the epidural catheter.

7. The epidural introducer assembly of claim 1 wherein the introducer needle is comprised of a radio-opaque material.

8. The epidural introducer assembly of claim 1 wherein the inner stylet is comprised of a radio-opaque material.

9. The epidural introducer assembly of claim 1 wherein the flexible outer sheath is comprised of a radio-opaque material.

10. The epidural introducer assembly of claim 1 wherein the flexible outer sheath has a lubricious or hydrophilic coating.

11. The catheter system of claim 1 wherein the epidural catheter has an exterior shaft braided with stainless steel wire.

12. The catheter system of claim 1 wherein at least one of the components comprising the catheter system comprises at least one of the following materials:
   (a) braided Peebax 31 pic Continuos;
   (b) braided Peebax 45 pic Continuos;
   (c) braided Polyurethane Continuos;
   (d) non-braided Peebax;
   (e) braided Peebax with polytetra Fluoroethelene liner;
   (g) a radiopaque guide wire;
   (h) a non-radiopaque guidewire;
   (i) a spray-coated guidewire; and
   a pretreated guidewire.

13. A method for introducing, guiding and removing medical devices in an epidural space using a catheter system comprising the steps of:
   (a) introducing percutaneously into the epidural space of a patient a one-piece introducer assembly comprising a flexible outer sheath and cannula connected to an introducer needle and an inner stylet;
   (b) removing the inner stylet to confirm placement in the epidural space;
   (c) unlocking and withdrawing the introducer needle away from the flexible outer sheath and cannula which remain placed in the epidural space of the patient; and
   (d) introducing or maneuvering through the flexible outer sheath a single or multiple piece catheter having or not having a soft tip.

14. The method of claim 13 additionally comprising the step of withdrawing at least one component of the introducer assembly from the epidural space while the catheter remains in the epidural space and removing by peeling a peelable sheath for long term injection through the epidural catheter.

15. The method of claim 13 additionally comprising the step of withdrawing at least one component of the introducer assembly from the epidural space while the catheter remains in the epidural space for long term injection through the epidural catheter.

16. The method of claim 13 additionally comprising the step of selecting components of the catheter system to comprise at least one of the following:
(a) braided Peebax 31 pic Continuos;
(b) braided Peebax 45 pic Continuos;
(c) braided Polyurethane Continuos;
(d) non-braided Peebax;
(e) braided Peebax with polytetra fluorocthelene liner;
(g) a radiopaque guidewire;
(h) a non-radiopaque guidewire;
(i) a spray coated guidewire; and
(j) a pretreated guidewire.

17. A method for precisely guiding an epidural catheter with or without a soft tip comprising the steps of:
(a) providing an elongated reinforced or non-reinforced one-piece or multiple piece epidural catheter with the distal end having catheter side holes or an open end and a proximal end connected to a fitting for the administration of medication and media to facilitate patients comfort and procedure time reduction;
(b) providing an epidural catheter of sufficient length to minimize radiation exposure to the practitioner;
(c) inserting a flexible guidewire into the central lumen of the catheter;
(d) reducing the catheter and/or guidewire shearing and/or scraping while advancing and/or withdrawing said components; and
(e) connecting a manifold adapter to the epidural catheter hub whereby the guidewire remains in place during injection of medications and contrast media.

18. A method as defined in claim 17 comprising the additional steps of:
(a) using a catheter and/or guidewire having a straight angled or curved tip configuration; and
(b) using a catheter and guidewire tip either or both being radiopaque and non-radiopaque.

19. A method for precisely guiding an epidural catheter with or without a soft tip comprising the steps of:
(a) providing an elongated reinforced or non-reinforced one-piece or multiple piece epidural catheter with a distal end having catheter side holes or an open end and a proximal end connected to a fitting for administration of medication and media to facilitate patients comfort and procedure time reduction;
(b) providing an epidural catheter of sufficient length to minimize radiation exposure to a practitioner;
(c) inserting a flexible guidewire into the central lumen of the catheter;
(d) reducing the catheter and/or guidewire shearing and/or scraping while advancing and/or withdrawing said components; and
(e) placing a torquing device on the guidewire to precisely guide the catheter into diseased areas of a spinal column and selective nerve roots.

20. method as defined in claim 17 further comprising the additional steps of:
(a) fluoroscopically monitoring the position of the introducer, catheter and guidewire in the epidural space.

* * * * *